United States Patent [19]

Suzuki et al.

[11] Patent Number: 5,397,319

[45] Date of Patent: Mar. 14, 1995

[54] GARMENT ABSORBENT STRUCTURE

[75] Inventors: Migaku Suzuki, Kamakura; Hiroaki Fukui, Kawaguchi, both of Japan

[73] Assignee: Paragon Trade Brands, Inc., Federal Way, Wash.

[21] Appl. No.: 99,072

[22] Filed: Jul. 28, 1993

[30] Foreign Application Priority Data

Dec. 4, 1992 [JP] Japan .................. 4-350204

[51] Int. Cl.6 ............................................. A61F 13/15
[52] U.S. Cl. ................... 604/385.2; 604/397
[58] Field of Search .................. 604/385.2, 358, 387, 604/393

[56] References Cited

U.S. PATENT DOCUMENTS

| | | | |
|---|---|---|---|
| 4,681,577 | 7/1957 | Stern et al. | |
| 4,701,177 | 10/1987 | Ellis et al. | 604/385.2 |
| 4,778,459 | 10/1988 | Fuisz. | |
| 5,167,654 | 12/1992 | Yang. | |
| 5,171,236 | 12/1992 | Drier et al. | |
| 5,295,987 | 3/1994 | Widlund et al. | 604/385.2 |
| 5,304,160 | 4/1994 | Igaue et al. | 604/385.2 |

FOREIGN PATENT DOCUMENTS

570016A1 5/1993 European Pat. Off. .

*Primary Examiner*—Jerome L. Kruter
*Attorney, Agent, or Firm*—Dressler, Goldsmith, Shore & Milnamow, Ltd.

[57] ABSTRACT

An absorbent structure in accordance with the present invention comprises a flexible shaped member having a raised peripheral rim to form a containment space for receiving body exudates. The shaped member comprises a first portion, and a second portion extending rearwardly from a rear end of the first portion. The first portion has along its side edges symmetrical indentations so that the first portion has a plan configuration including a generally rectangular front segment, and inwardly contoured side edges respectively extending rearwardly from the front segment in a diverging manner into the second portion. The second portion has a generally rectangular plan configuration wider than the first portion, so that the shaped member has a generally anvil-shaped, overall plan configuration. The absorbent structure further comprises absorbent material disposed in the first portion. The absorbent material is absent in the second portion to leave a void space therein for receiving fecal material. A liquid permeable top sheet overlies the shaped member for covering the containment space thereof.

8 Claims, 1 Drawing Sheet

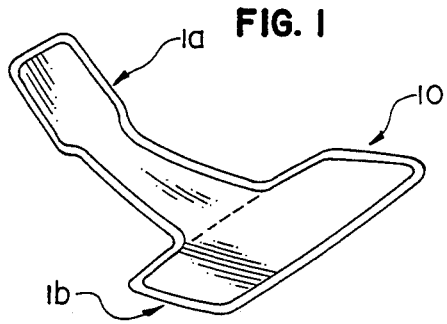
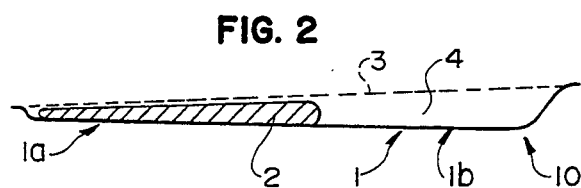
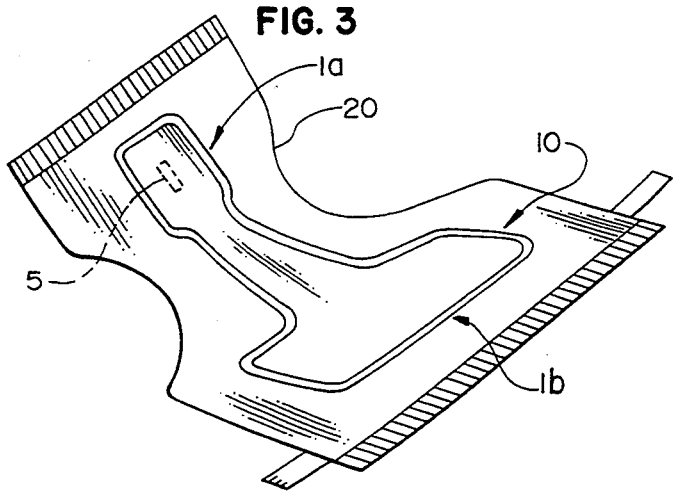
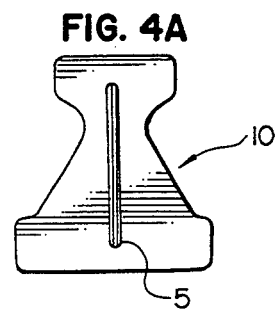
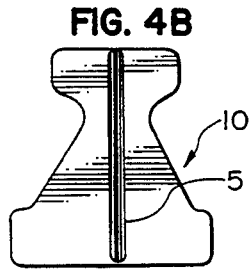
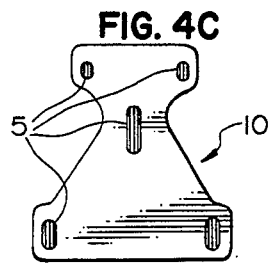
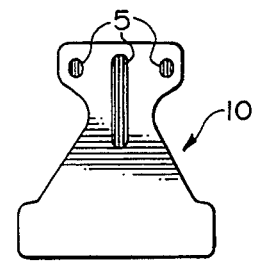
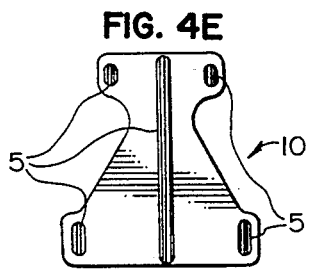
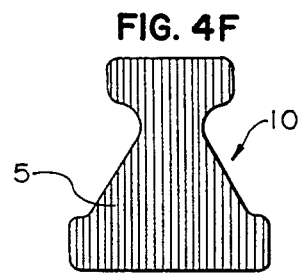
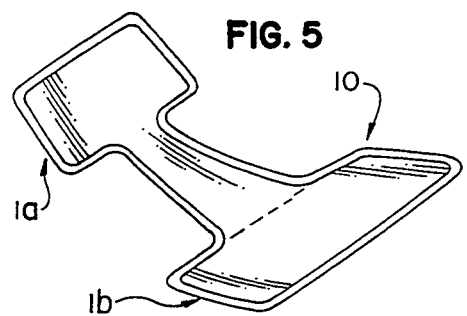

GARMENT ABSORBENT STRUCTURE

FIELD OF THE INVENTION

The present invention relates to an absorbent structure having discrete, urine and fecal material receiving areas therein, and further relates to an absorbent garment, such as an infant diaper or an adult diaper, integrally incorporating such an absorbent structure.

BACKGROUND OF THE INVENTION

Absorbent garments, such as infant diapers and adult diapers, typically include a large area of an absorbent structure in a selected position therein. Such absorbent garments further include a liquid impermeable backing sheet and a liquid permeable cover sheet between which the absorbent structure is interposed for receiving and holding therein body exudates including urine and fecal material.

Over the years, a number of techniques have been proposed to improve urine containment characteristics of absorbent structures. However, few absorbent structures have met with satisfactory fecal material containment capability. Most typically, such flat absorbent structures are disadvantageously shifted from their desired initial position relative to a wearer's body in accordance with the movement of the wearer's body. Consequently, such constructions fail to hold the body exudates therein, with the result that it provides a uncomfortable feeling to the wearer during use and also the body exudates leak from sides of the garment.

It is an object of the present invention to provide an absorbent structure which is configured to better conform to the wearer's body, and is capable of receiving and holding urine and fecal material in discrete areas therein.

It is another object of the present invention to provide an absorbent garment which integrally incorporates such an absorbent structure in a desired manner.

SUMMARY OF THE INVENTION

An absorbent structure in accordance with the present invention comprises a flexible shaped member having a raised peripheral rim to form a containment space for receiving body exudates. The shaped member comprises a first portion, and a second portion extending rearwardly from a rear end of the first portion. The first portion has along its side edges symmetrical indentations so that the first portion has a plan configuration including a generally rectangular front segment, and inwardly contoured side edges respectively extending rearwardly from the front segment in a diverging manner into the second portion. The second portion has a generally rectangular plan configuration wider than the first portion, so that the shaped member has a generally anvil-shaped, overall plan configuration.

The absorbent structure further comprises absorbent material disposed in the first portion. The absorbent material is absent in the second portion to leave a void space therein for receiving fecal material. A liquid permeable top sheet overlies the shaped member for covering the containment space thereof.

In one embodiment of the present invention, a top surface of the raised peripheral rim slopes upwardly from a front end of the first portion toward a rear end of the second portion, so that the containment space of the shaped member is formed deeper in a rearward direction.

The present invention further provide an absorbent garment which comprises a liquid impermeable outer cover for encircling a wearer's body, and a flexible, shaped member integrally connected onto the outer cover. The flexible shaped member has a raised peripheral rim to form a containment space for receiving body exudates. The shaped member comprises a first portion, and a second portion extending rearwardly from a rear end of the first portion. The first portion has along its side edges symmetrical indentations so that the first portion has a plan configuration including a generally rectangular front segment, and inwardly contoured side edges respectively extending rearwardly from the front segment in a diverging manner into the second portion. The second portion has a generally rectangular plan configuration wider than the first portion, so that the shaped member has a generally anvil-shaped, overall plan configuration.

The absorbent garment further comprises absorbent material disposed in the first portion. The absorbent material is absent in the second portion to leave a void space for receiving fecal material therein. A liquid permeable top sheet overlies the shaped member for covering the containment space thereof.

Numerous other advantages and features of the present invention will become readily apparent from the following detailed description, the appended drawings, and the accompanying claims.

BRIEF DESCRIPTION OF THE DRAWINGS

FIG. 1 is a perspective view of an absorbent structure embodying the principles of the present invention;

FIG. 2 is a longitudinal cross-sectional view of the absorbent structure of FIG. 1;

FIG. 3 is a perspective view of an absorbent garment incorporating the absorbent structure of FIG. 1;

FIGS. 4A through 4F are explanatory views illustrating various arrangements of the regions of securement for attaching the absorbent structures to the outer cover, respectively; and FIG. 5 is a perspective view of another embodiment of the absorbent structure in accordance with the present invention.

DETAILED DESCRIPTION

While the present invention is susceptible of embodiments in various forms, there are shown in the drawings and will hereinafter be described various embodiments of the invention, with the understanding that the present disclosure is to be considered as an exemplification of the invention, and is not intended to limit the invention to the specific embodiments illustrated and described herein.

FIG. 1 is a perspective view of an absorbent structure in accordance with the present invention. FIG. 2 is a longitudinal cross-sectional view of the absorbent structure of FIG. 1. An absorbent structure 10 comprises a shaped member 1, an absorbent material 2 supported on the shaped member 1, and a top sheet 3 disposed to cover a whole interior space of the shaped member 1.

In the illustrated embodiment, the shaped member 1 comprises a first portion 1a, and a second portion 1b extending rearwardly from a rear end of the first portion. The second portion 1b is of generally rectangular shaped, plan configuration. The second portion 1b is formed wider than the first portion 1a and is sized and configured to conform to and cover a rear crotch portion of a wearer. As best seen from FIG. 4, the first portion 1a has along its opposite side edges symmetrical concave indentations, so that the first portion 1a has a plan configuration including a generally rectangular, front segment, and inwardly contoured side edges respectively extending rearwardly from the front segment in a diverging manner into the second portion 1b. Accordingly, the shaped member 1 has a generally anvil-shaped, overall plan configuration.

The shaped member 1 has a raised peripheral rim to form a tray-like, three-dimensional containment configuration for receiving body exudates. As best seen from FIG. 2, a top surface of the raised peripheral rim slopes upwardly from a front end of the first portion 1a toward a rear end of the second portion 1b, so that the containment space of the shaped member 1 is formed deeper in a rearward direction.

The shaped member 1 may have a generally flat configuration, in side view, as illustrated in FIG. 2. Preferably, the shaped member 1 has a curved configuration, in side view, which in combination with the sloped top surface of the raised peripheral rim, to further conforms the shaped member 1 to a crotch portion of the wearer. Suitable materials for the shaped member 1 include polymer foam materials, such as polyurethane foam and polyethylene foam, which are sufficiently flexible or resilient to retain a preformed curved configuration, in side view, of the shaped member 1.

The absorbent material 2 is disposed in the first portion 1a and extends from the front end of the first portion to about to a midpoint along the length of the shaped member, as seen in FIG. 2. The absorbent material 2 is covered by the liquid permeable top sheet 3 for receiving and absorbing liquids such as urine. The absorbent material 2 may comprise hydrophilic materials such as wood pulp and cotton, or hydrophilized synthetic fibers such as polypropylene and polyester fibers. The absorbent material 2 may preferably comprise superabsorbent polymer which is capable of absorbing several times their weight of liquids.

The absorbent material 2 is not disposed in the second portion 1b, so that a void space is formed therein for receiving fecal material.

The absorbent structure 10 thus constructed is applied to a crotch portion of a wearer, typically with aid of a separate, liquid impermeable outer cover which encircles waist portions of the wearer. Any body movement of the wearer does not substantially change the desired positioning of the absorbent structure 10 relative to the wearer's body since it is not connected to the outer cover.

FIG. 3 illustrates an absorbent garment comprising a disposable diaper which comprises an outer cover 20, and the absorbent structure 10, as shown in FIGS. 1 and 2, integrally connected to the outer cover 20. The outer cover 20 may comprise any component known in the art, such as a diaper cover or holder. In the embodiment of FIG. 3, the absorbent structure 10 is connected or secured to the outer cover 20 at a region of securement 5 as illustrated by a broken line, by means of any suitable securement means such as hot melt adhesives. As seen from FIG. 3, the first portion 1a of the absorbent structure 10 is at its underface secured to a front section of the outer cover 20 through the narrow elongated region of securement 5, so that the absorbent structure 10 is at its front end supported by the outer cover 20, as if connected in a suspended manner. This permits the absorbent structure 10 and the outer cover 20 to move relative to each other with less restriction. Accordingly, when the outer cover 20 is constructed from an elastically stretchable material, such stretchability of the outer cover 20 is substantially fully utilized in an advantageous manner.

FIGS. 4A through 4E illustrate variant patterns of the region(s) of securement 5 which permit the stretchable outer cover 20 to fully exhibit its flexibility or stretchability. The region of securement 5 comprises a longitudinally elongated, center region of securement in FIG. 4A. The center region of securement extends over substantially the full length of the shaped member 1 in FIG. 4B. In FIGS. 4C through 4E, the regions of securement 5 comprise selected combinations of the center region, laterally spaced, first regions on opposite side ends of the front segment of the first portion 1a, and/or laterally spaced, second regions on opposite side ends of the second portion 1b. FIG. 4F illustrates another embodiment wherein the absorbent structure 10 is secured at its entire area to the nonstretchable outer cover by a plurality of parallel lines of securement 5.

Such an integral absorbent garment is applied to a wearer so that the absorbent structure 10 is properly positioned to fit in the crotch portion of the wearer. It is preferable that the absorbent structure 10 has a narrow, longitudinal intermediate portion to fit better to the crotch portion. FIG. 5 illustrates another embodiment wherein the first portion 1a is formed wider to increase the absorbent capacity thereof. From the foregoing, it will be observed that numerous modifications and variations can be effected without departing from the true spirit and scope of the novel concept of the present invention. It is to be understood that no limitation with respect to the specific embodiments illustrated herein is intended or should be inferred. The disclosure is intended to cover by the appended claims all such modifications as fall within the scope of the claims.

What is claimed is:

1. An absorbent structure comprising:

a flexible shaped member having a raised peripheral rim to form a containment space for receiving body exudates, said shaped member comprising a first portion, and a second portion extending rearwardly from a rear end of the first portion, said raised peripheral rim extending about said first portion and said second portion, said first portion having along its side edges symmetrical indentations so that the first portion has a plan configuration including a generally rectangular front segment, and inwardly contoured side edges respectively extending rearwardly from the front segment in a diverging manner into the second portion, said second portion having a generally rectangular plan configuration wider than the first portion such that said second portion extends laterally of a longitudinal centerline of said shaped member more than the lateral extent of said first portion, so that said shaped member has a generally anvil-shaped, overall plan configuration; wherein a top surface of said raised peripheral rim slopes upwardly from a front end of the first portion toward a rear end of the second portion, so that the containment space of the shaped member is formed deeper in a rearward direction;

an absorbent material disposed in said first portion, said absorbent material being absent in the second portion to leave a void space for receiving fecal material therein; and a liquid permeable top sheet overlaying said shaped member for covering the containment space thereof.

2. The absorbent structure of claim 1, wherein
a top surface of said raised peripheral rim slopes upwardly from a front end of the first portion toward a rear end of the second portion, so that the containment space of the shaped member is formed deeper in a rearward direction.

3. The absorbent structure of claim 1, wherein
said absorbent material is disposed extending from said front end of the first portion to about a midpoint along the length of the shaped member.

4. The absorbent structure of claim 3, wherein
said absorbent material comprises superabsorbent polymer.

5. An absorbent garment comprising:
a liquid impermeable outer cover for encircling a wearer's body;
a flexible shaped member integrally connected onto said outer cover, said flexible shaped member having a raised peripheral rim to form a containment space for receiving body exudates, said shaped member comprising a first portion, and a second portion extending rearwardly from a rear end of the first portion, said raised peripheral rim extending about said first portion and said second portion, said first portion having along its side edges symmetrical indentations so that the first portion has a plan configuration including a generally rectangular front segment, and inwardly contoured side edges respectively extending rearwardly from the front segment in a diverging manner into the second portion, said second portion having a generally rectangular plan configuration wider than the first portion such that said second portion extends laterally of a longitudinal centerline of said shaped member more than the lateral extent of said first portion, so that said shaped member has a generally anvil-shaped, overall plan configuration, said peripheral rim extending upwardly from said second portion more than from said front segment of said first portion, so that the containment space of the shaped member is deeper in the second portion than in the front segment of said first portion;

an absorbent material disposed in said first portion, said absorbent material being absent in the second portion to leave a void space for receiving fecal material therein; and a liquid permeable top sheet overlaying said shaped member for covering the containment space thereof.

6. The absorbent garment of claim 5, wherein
said shaped member is at its entire area secured to the outer cover by a plurality of parallel lines of securement.

7. The absorbent garment of claim 5, wherein
said first portion of the shaped member is secured to a front section of the outer cover through one or more narrow regions of securement, so that the shaped member is at its front end supported by the outer cover.

8. The absorbent garment of claim 7, wherein
said outer cover is elastically stretchable.

* * * * *